United States Patent
Lucas et al.

(10) Patent No.: US 6,640,459 B1
(45) Date of Patent: Nov. 4, 2003

(54) MULTIDIMENSIONAL CONTACT MECHANICS MEASUREMENT SYSTEM

(75) Inventors: Barry N. Lucas, Maryville, TN (US); John C. Hay, Jr., Knoxville, TN (US)

(73) Assignee: Fast Forward Devices, LLC, Knoxville, TN (US)

( * ) Notice: Subject to any disclaimer, the term of this patent is extended or adjusted under 35 U.S.C. 154(b) by 0 days.

(21) Appl. No.: 09/784,494

(22) Filed: Feb. 15, 2001

(51) Int. Cl.⁷ .................................................. G10B 3/14
(52) U.S. Cl. ............................. 33/552; 33/558; 33/561
(58) Field of Search ........................ 33/552, 549, 551, 33/553, 554, 555, 556, 558, 559, 561

(56) References Cited

U.S. PATENT DOCUMENTS

| | | | | |
|---|---|---|---|---|
| 3,869,799 A | * | 3/1975 | Neuer et al. ............... 33/23.11 |
| 4,343,993 A | | 8/1982 | Binnig et al. |
| 4,465,741 A | * | 8/1984 | Yamatsuta et al. ........... 428/608 |
| 4,611,403 A | * | 9/1986 | Morita et al. ................ 33/558 |
| 4,866,854 A | * | 9/1989 | Seltzer ......................... 33/558 |
| 4,934,065 A | * | 6/1990 | Hajdukiewicz et al. ....... 33/561 |
| 4,972,597 A | * | 11/1990 | Kadosaki et al. ............. 33/556 |
| 5,040,306 A | * | 8/1991 | McMurtry et al. ............ 33/503 |
| 5,051,594 A | * | 9/1991 | Tsuda et al. ............ 250/442.11 |
| 5,116,782 A | * | 5/1992 | Yamaguchi et al. ..... 250/492.3 |
| 5,223,713 A | * | 6/1993 | Uozumi et al. ............. 250/306 |
| 5,283,437 A | * | 2/1994 | Greschner et al. ......... 250/306 |
| 5,304,172 A | | 4/1994 | Manoukian et al. .......... 606/15 |
| 5,384,507 A | * | 1/1995 | Takada et al. ............... 310/317 |
| 5,410,151 A | * | 4/1995 | Buckland ............... 250/227.11 |
| 5,509,211 A | * | 4/1996 | Ernst ............................ 33/558 |
| 5,524,354 A | | 6/1996 | Bartzke et al. ............... 33/561 |
| 5,594,995 A | * | 1/1997 | Matsuhashi .................. 33/558 |
| 5,623,766 A | * | 4/1997 | Ruck et al. .................. 33/559 |
| 5,778,551 A | * | 7/1998 | Herklotz et al. ............. 33/503 |
| 5,797,191 A | | 8/1998 | Ziegert ......................... 33/503 |
| 5,861,954 A | | 1/1999 | Israelachvili |
| 5,884,410 A | | 3/1999 | Prinz .......................... 33/559 |
| 5,960,553 A | | 10/1999 | Ishii et al. ..................... 33/556 |
| 5,994,820 A | * | 11/1999 | Kleindiek .................... 310/329 |
| 6,163,974 A | * | 12/2000 | Masek et al. ................ 33/1 PT |
| 6,292,610 B1 | * | 9/2001 | O'Rourke et al. ............. 385/52 |
| 6,295,866 B1 | * | 10/2001 | Yamamoto et al. ....... 33/501.04 |
| 6,314,800 B1 | * | 11/2001 | Nishimura .................... 33/551 |
| 6,360,176 B1 | * | 3/2002 | Nishioki et al. .............. 702/56 |
| 6,367,159 B1 | * | 4/2002 | Naoi et al. ............... 33/501.02 |

OTHER PUBLICATIONS

Chen, C. Julian, Introduction to Scanning Tunneling Microscopy, 1993, p. 221–224, Oxford University Press, New York, NY, USA.

Binnig, G., Rohrer, H., Gerber, C., Weibel, E., Surface studies by scanning tunneling microscopy, Physical Review Letters, Jul. 5, 1982, 57–61, vol. 49, No. 1.

Binnig, G. and Rohrer, H., Scanning tunneling microscopy, Helvetica Physica Acta, 1982, 726–735, vol. 55.

* cited by examiner

Primary Examiner—Christopher W. Fulton
Assistant Examiner—Amy R. Cohen
(74) Attorney, Agent, or Firm—Luedeka, Neely & Graham, P.C.

(57) ABSTRACT

A multidimensional surface mechanics measurement system applies forces to a surface while minimizing coupling between the forces so applied. The system includes first, second, and third elongate members, a coupler for coupling the elongate members together, and a probe connected to the coupler having a contact point for contacting the surface. The first elongate member extends in a first axial direction that is substantially normal to the surface, the second elongate member extends in a second axial direction that is substantially orthogonal to the first axial direction, and the third elongate member extends in a third axial direction that is substantially orthogonal to the first and second axial directions. Desired relationships between the free length and diameter, and between the axial stiffness and transverse stiffness, and the orthogonal relative positioning of the elongate members, minimizes cross-talk between the measurement axes while maintaining the necessary structural rigidity.

21 Claims, 17 Drawing Sheets

MULTIDIMENSIONAL CONTACT
MECHANICS MEASUREMENT SYSTEM

TECHNICAL FIELD

The present invention is generally directed to an apparatus for conducting contact mechanics measurements in multiple dimensions. More particularly, the invention is directed to a system for coupling three orthogonal one-dimensional force and displacement measuring systems for conducting contact mechanics measurements on a surface, where forces on the surface in any two orthogonal directions resulting from the application of a force in the third direction are minimized.

BACKGROUND OF THE INVENTION

Many industries utilize thin and hard coatings that are scratch or wear resistant to extend the lifetime of their products or devices. Such industries have historically depended heavily on instrumented indentation for mechanical characterization of these coatings. These industries include the rigid magnetic storage (computer hard disk) industry, the flexible magnetic storage (VCR/Tape) industry, the optical coatings industry, the automotive (paint and chrome) industry, and the orthopedic industry. In many of these industries, particularly those involved with magnetic storage and retrieval, the thickness of these coatings has continually decreased over the past decade as the demands for increased performance have forced storage densities to increase.

As coatings have become thinner, many of the typical contact mechanics techniques used in the past in attempts to characterize such coatings have become obsolete. For example, depth-sensing indentation systems provide little if any meaningful information concerning coating properties in the plane of the coating. Although atomic force microscope systems have been used in attempts to gather mechanical information on properties of thin surface coatings in the plane of the surface, these systems are lacking in their ability to provide meaningful information due at least in part to coupling, also referred to herein as cross-talk, between different axes of measurement.

What is needed, therefore, is a contact mechanics measurement system that minimizes cross-talk between orthogonal measurement axes, so that forces and displacements in directions both normal to the coating surface as well as in the plane of the surface may be measured quantitatively.

SUMMARY OF THE INVENTION

The foregoing and other needs are met by a multidimensional surface mechanics measurement system for applying forces to a surface or imposing displacements of a surface from multiple directions and for minimizing coupling between the forces or displacements so applied. The system includes at least a first elongate member, a second elongate member, a coupler for coupling the first elongate member to the second elongate member, and a probe which is connected to the coupler and which has a contact point for contacting the surface. The first elongate member extends in a first axial direction, which in a preferred embodiment, is substantially normal to the surface. The second elongate member extends in a second axial direction that is substantially orthogonal to the first axial direction. The coupler includes structures for attaching the first and second elongate members to the coupler such that the second elongate member is disposed substantially orthogonal to the first elongate member when attached to the coupler.

Preferred embodiments of the system include a third elongate member extending in a third axial direction that is substantially orthogonal to the first and second axial directions. The coupler of these preferred embodiments includes a structure for attaching the third elongate member to the coupler, such that the third elongate member is disposed substantially orthogonal to the first and second elongate members.

Preferably, the free length of the elongate members ranges from about 12.7 mm to about 25.4 mm, the diameter of the elongate members ranges from about 400 μm to about 440 μm, and the ratio of free length to diameter of the elongate members ranges from about 37 to about 45. Preferably, the ratio of axial stiffness to transverse stiffness for each of the elongate members ranges from about 3,000 to 30,000, and is most preferably about 10,000. The elongate members are preferably formed from a material having a Young's modulus of approximately 10 GPa to 500 GPa, and a coefficient of thermal expansion of approximately $1.0 \times 10^{-7}$ m/°C. to $1.0 \times 10^{-5}$ m/°C. These relationships between axial and transverse properties, as well as the relative positioning of the elongate members, provides for minimization of cross-talk between the measurement axes while maintaining the structural rigidity necessary to perform contact mechanics measurements. Thus, the system provides for accurate and quantitative measurement of forces and displacements in directions both normal to a surface, as well as in the plane of the surface.

In some preferred embodiments of the system, the coupler includes a first rigid member aligned with the first axial direction, a second rigid member aligned with the second axial direction, and a third rigid member aligned with the third axial direction. The structure for attaching the first elongate member to the coupler includes a first shaft into which a first end of the first elongate member is inserted. The structure for attaching the second elongate member to the coupler includes a second shaft into which a first end of the second elongate member is inserted. The structure for attaching the third elongate member to the coupler includes a third shaft into which a first end of the third elongate member is inserted. In these preferred embodiments, the first ends of the first, second, and third elongate members have outside diameters of substantially equal to but no greater than the inside diameters of the first, second, and third shafts, respectively.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows.

DETAILED DESCRIPTION OF THE PREFERRED EMBODIMENTS

Figure 1:
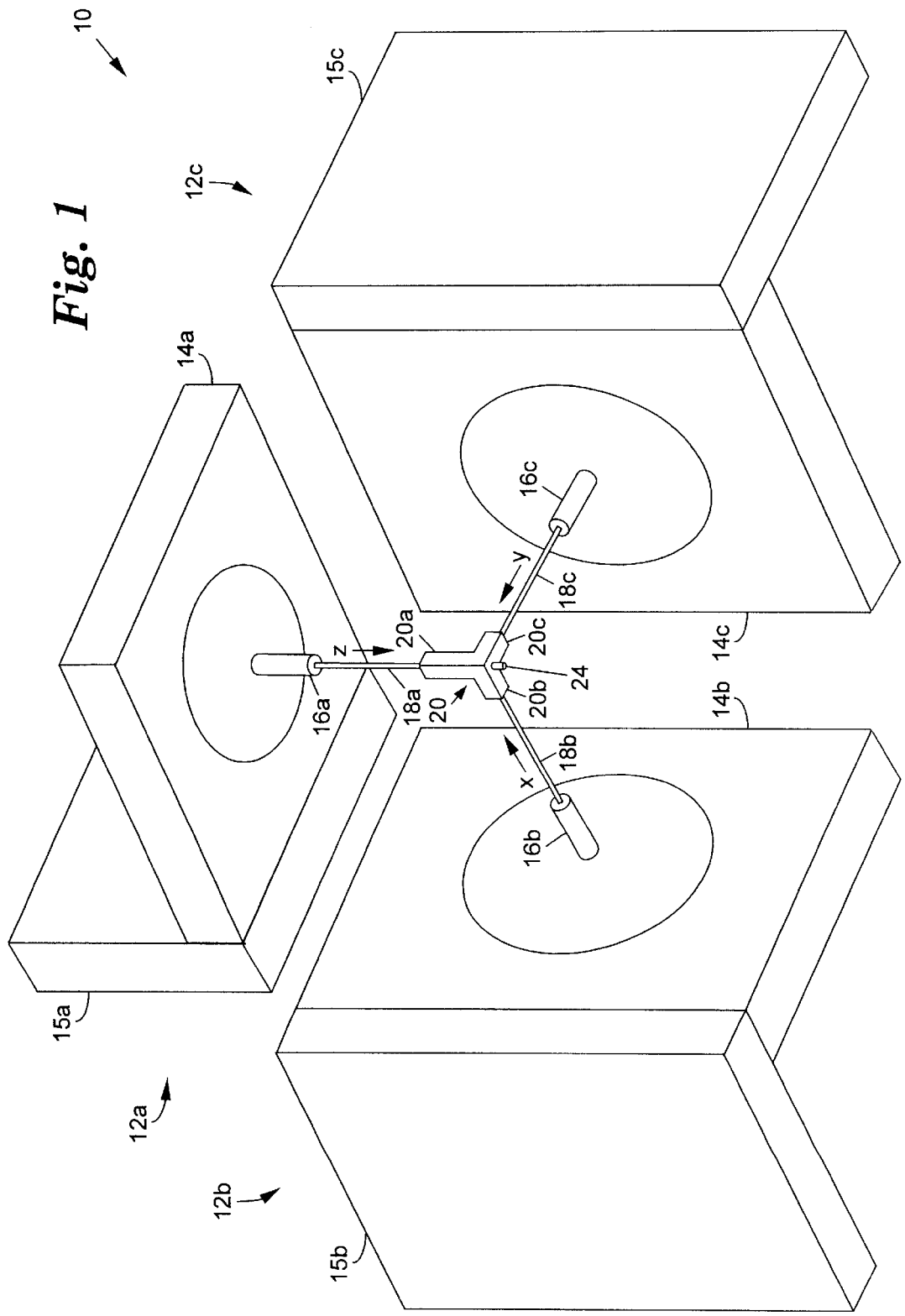
FIGS. 1 and 2 are perspective views of a multidimensional contact mechanics measurement system according to a preferred embodiment of the invention.

Shown in FIG. 1 is a contact mechanics measurement system 10 consisting of three, one-dimensional force generating/displacement measuring subsystems 12a, 12b, and 12c that are coupled together to provide three independent axes of motion. The subsystems 12a, 12b, and 12c each include a one-dimensional actuator 14a, 14b, and 14c mounted along the z, x, or y measurement axis, respectively. In the preferred embodiment, the actuators 14a–c are Dynamic Contact Modules manufactured by MTS Systems Corporation, Nano Instruments Innovation Center, Oak Ridge, Tenn. 37830. Preferably, an independent coil-in-magnet assembly controls the force for each actuator. However, any means of a force application, including but not limited to electrostatic actuation, pneumatic actuation, or piezoelectric actuation, that provides a substantially linear motion in the direction of actuation is acceptable. It should also be noted that the method of actuation is not limited to force-controlled actuators but could alternatively be an actuator that is inherently displacement controlled in nature. It is also important that the actuators 14a–c be rigid in the two directions transverse to the direction of actuation, such that all off-axis displacement is confined to the mechanism that couples the three axes, as described in more detail below.

In the preferred embodiment, the individual actuators 14a–c are mounted to rigid aluminum brackets 15a–c designed to hold the three actuators 14a–c at right angles when fixed securely together. Preferably, the brackets 15a–c are attached to an interconnected structure (not shown) in such a fashion as to allow the brackets 15a–c to slide into place along their corresponding axes. This allows assembly of the three subsystems 12a–c in a sequential manner as described below.

Each subsystem 12a–c preferably includes an independent system for measuring the linear displacement of the associated actuator 14a–c. In the preferred embodiment, the displacement measurement is made using a three plate capacitive system. However, any means for displacement measurement of sufficient resolution, including but not limited to, laser interferometers, fiber optic displacement sensors, capacitance probes, or non-contact eddy current displacement measuring systems, is acceptable. Preferably, each axis of actuation is independently controlled by control electronics that continuously monitor a voltage related to the force being exerted by the actuator 14a–c and the displacement of the actuator 14a–c. While the force application system and the displacement measuring system are important from the aspect that each must have the ability to measure the desired quantities to an appropriate resolution, one skilled in the art will appreciate that this aspect of the system could be constructed from a number of commercially available force-generating and displacement-measuring systems, such as those manufactured by Hysitron, Inc., Instron, Inc., the Swiss Center for Electronics and Microtechnology (CSEM), or CSIRO of Australia, and that the scope of the invention is not limited to any particular configuration of systems for measuring force and displacement.

As shown in FIG. 1, a coupling mechanism, such as an Invar tube 16a–c, is attached to the loading column of each actuator 14a–c, with the axis of each actuator tube 16a–c parallel to the associated displacement axis. In the preferred embodiment, each tube 16a–c has a cylindrical axial hole with a diameter of about 430 to 440 $\mu$m, and most preferably about 435 $\mu$m, for receiving one of three fibers 18a–c, as described below.

The preferred embodiment of the system 10 includes three fused silica cylindrical fibers 18a–c of about 15 to 18 mm in length, and each having a diameter of 415 to 425 $\mu$m, and most preferably about 420 $\mu$m. Although in the preferred embodiment, the fibers 18a–c are formed from silica, the fibers 18a–c could be formed from any material having a desired stiffness in the axial and transverse directions, as discussed in more detail hereinafter. Thus, it will be appreciated that the invention is not limited to any particular fiber material. The fibers 18a–c of the preferred embodiment are manufactured by Specialty Glass Products of Willow Grove, Pa.

Figure 2:
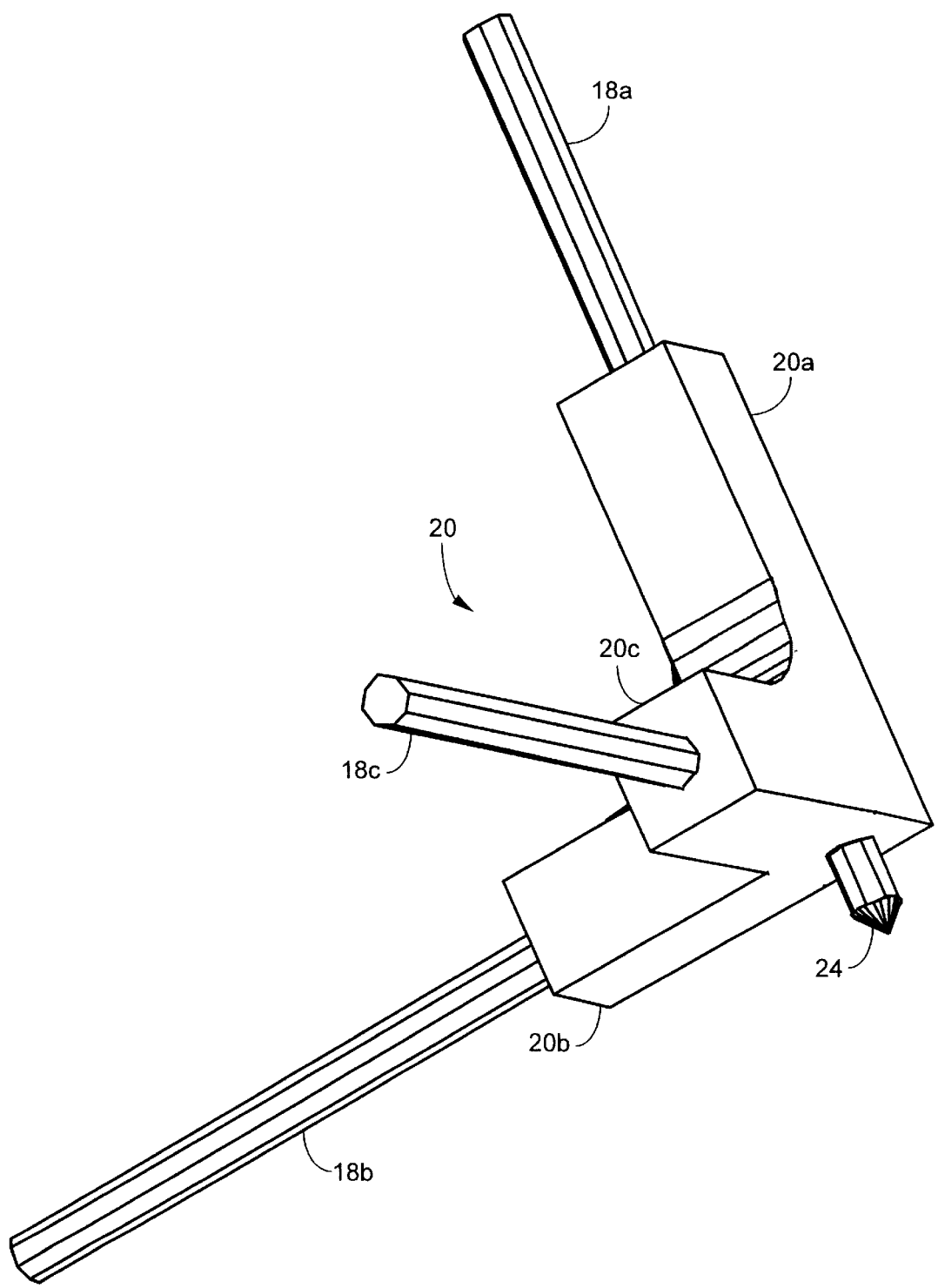
Figure 3A:
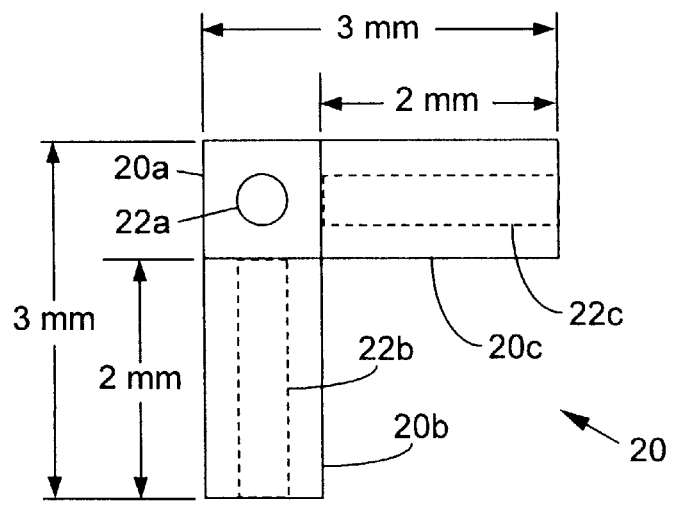
FIGS. 3A and 3B are top and side views of the multidimensional contact mechanics measurement system according to a preferred embodiment of the invention.
Figure 3B:
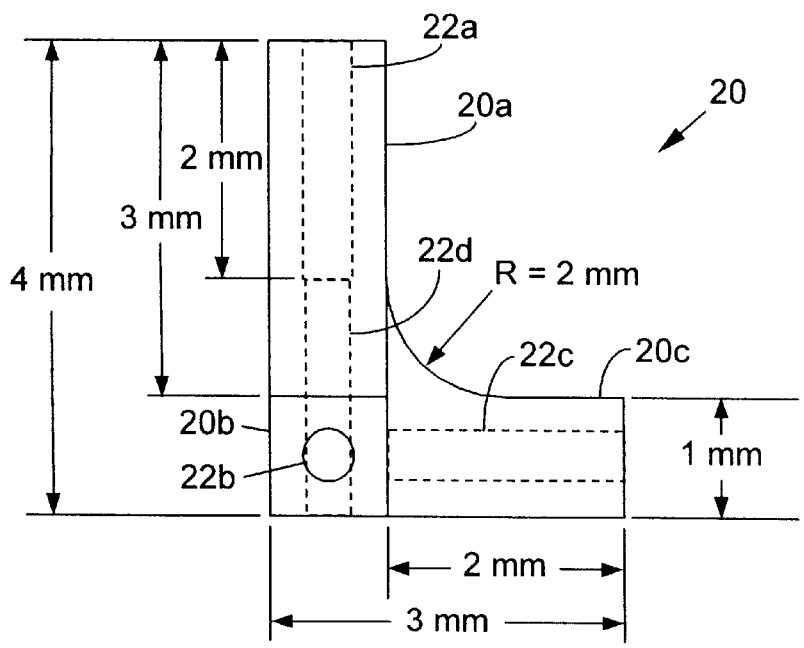

In a process as described below, one end of each fiber 18a–c is inserted into the axial hole of an associated one of the actuator tubes 16a–c to rigidly attach the fiber 18a–c thereto. The other end of each fiber 18a–c is connected to a three-dimensional coupler 20, as depicted in FIGS. 2 and 3A–B. In the preferred embodiment, the coupler 20 is machined from a single block of metal, such as aluminum, to form three rigid members 20a–c. Within each member 20a–c is a hole 22a–c, also referred to herein as a shaft, for receiving an associated one of the fibers 18a–c. Each hole 22a–c is drilled to a diameter of about 430 to 440 μm, and most preferably about 435 μm, and to a depth of about 1 to 3 mm, and most preferably about 2 mm. The ratio of the depth to the inside diameter of the each hole is preferably no less than approximately 4.8 A fourth hole 22d in the bottom of the coupler 20 is provided to accept a probe 24 for the contact measurements.

Although the coupler 20 of the preferred embodiment is formed from aluminum, it should be appreciated that other materials could be used, such as other metals or thermoplastics or composite materials, and that the invention is not limited to any particular coupler material. It should also be appreciated that the coupler 20 could take other shapes. For example, the coupler 20 could be in the form of a cube or block, with the holes 22a–c for receiving the fibers 18a–c formed in orthogonal faces of the cube. Also, other methods of securing the ends of the fibers 18a–c to the coupler 20 could be employed. For example the fibers 18a–c could be secured by brackets attached to orthogonal faces of a cube or other block.

The preferred embodiment of the invention is assembled according to the process described hereinafter. One skilled in the art will appreciate, however, that the system 10 may be assembled in other ways, and that the invention is not limited to any particular assembly process. First, the fibers 18a–c are cut to a starting length of approximately 25 mm, with the final length to be determined during later steps in the assembly procedure. The fibers 18a–c are inserted into the actuator tubes 16a–c and are fixed therein using a low flow point (121° C.) hot-wax (such as Crystal Bond manufactured by Aremco Products, Valley Cottage, N.Y.) that becomes quite rigid when cooled (modulus=3.1 GPa).

While viewed using an optical microscope, one of the silica fibers, such as fiber 18a, is inserted into the hole 22a in the coupler member 20a and is bonded using the hot wax. At the same time, the coupler 20 is rotated into the proper position to align the other holes 22b and 22c as closely as possible to accept the other two fibers 18b and 18c at the appropriate angles relative to the axis of the fiber 18a. This is preferably accomplished using soldering tweezers so that the temperature of the coupler 20 is maintained above the melting point of the hot wax.

The actuator 14b to which the second fiber 18b is connected is next slid into place such that the fiber 18b comes into the field of view under the optical microscope. The angle of the coupler 20 is then adjusted until the member 20b is oriented to accept the fiber 18b. Again, this is preferably accomplished by using the soldering tweezers to heat the coupler 20 to above the melting point of the hot wax. Next, using the soldering tweezers to heat the fiber 18b, the actuator 14b is slid into position such that the fiber 18b slides into the appropriate hole 22b in the coupler member 20b. The bracket 15b holding the actuator 14b is then firmly secured to the bracket 15a holding the actuator 14a.

The coupler 20 and the actuator tubes 16a and 16b holding the fibers 18a and 18b are then sequentially heated to allow the system to come to equilibrium. This is an important step as the elastic strain energy stored in the fibers 18a and 18b when they are not exactly aligned tends to self-align the system in this step. Once the two fibers 18a and 18b have come to equilibrium (where equilibrium is determined by observing that there is no further relaxation of the system when either the coupler 20 or the actuator tubes 16a and 16b are heated), the actuator 14c is slid into place until the fiber 18c comes into view under the optical microscope.

At this point, if the fiber 18c does not align properly with its respective hole 22c, the lengths of the fibers 18a and 18b are adjusted accordingly, and the preceding steps are repeated to adjust the orientation of the hole 22c with respect to the fiber 18c. When this alignment process is complete, the fiber 18c is heated, preferably with the soldering tweezers, and the actuator 14c is slid into place until the fiber 18c is seated in the hole 22c of the member 20c. The actuator 14c is then firmly secured in place relative to the actuators 14a and 14b. The process of sequentially heating the actuator tubes 16a–c and the coupler 20 is again repeated to allow the elastic strain energy stored in the fibers 18a–c to self-align the system.

The motion of the three actuators 14a–c is then tested to ensure that each axis is properly aligned and that smooth motion of the actuators 14a–c over their entire range of travel is observed. If all of the actuators 14a–c perform to specification, the final step of the process is to install the probe 24 into the coupler 20 as shown in FIG. 2. At this point, the system 10 is ready for final calibration and use.

Figure 4:
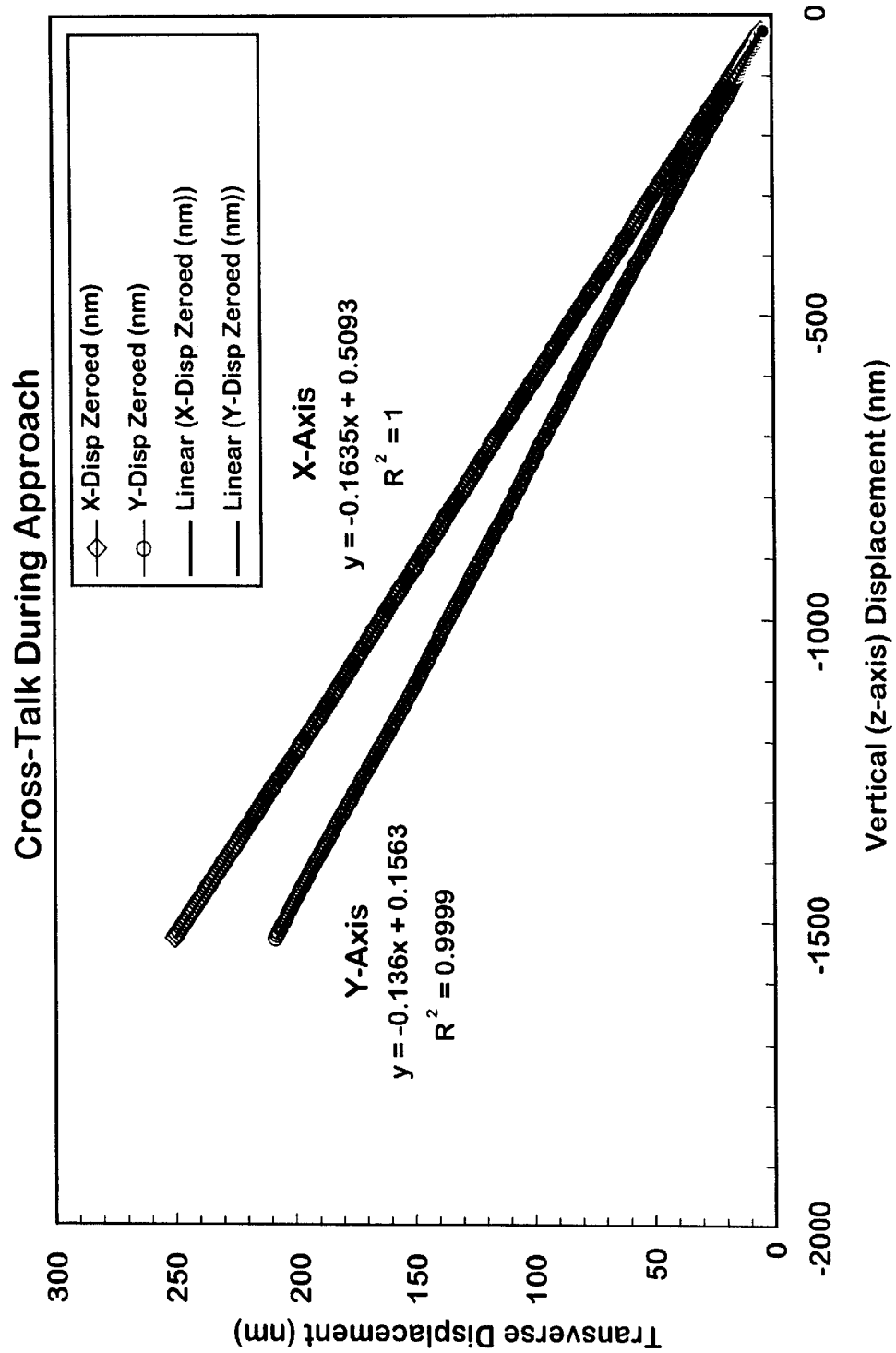
FIG. 4 is a graph depicting transverse displacement versus vertical displacement for x and y axes of the multidimensional contact mechanics measurement system, when the contact probe is not in contact with a surface, according to a preferred embodiment of the invention.

One of the most important aspects of the system 10 is that it minimizes cross-talk between the three orthogonal axes while maintaining the structural rigidity required to perform the desired contact mechanics measurements. The cross-talk between the axes may be characterized by monitoring the motion of two of the three axes while the third axis is moved over some range of displacements while the system is free to move in space, i.e., while the probe 24 is not contacting a surface. Shown in FIG. 4 is a plot of transverse displacement of the tip of the probe 24 in the x and y-axes, as a function of controlled motion of the z-axis actuator 14a. The slope of these data yield the fractional cross-talk between the axes. From these data, the cross-talk for the x and y axes is observed to be about 0.16 and 0.14 respectively.

Figure 5:
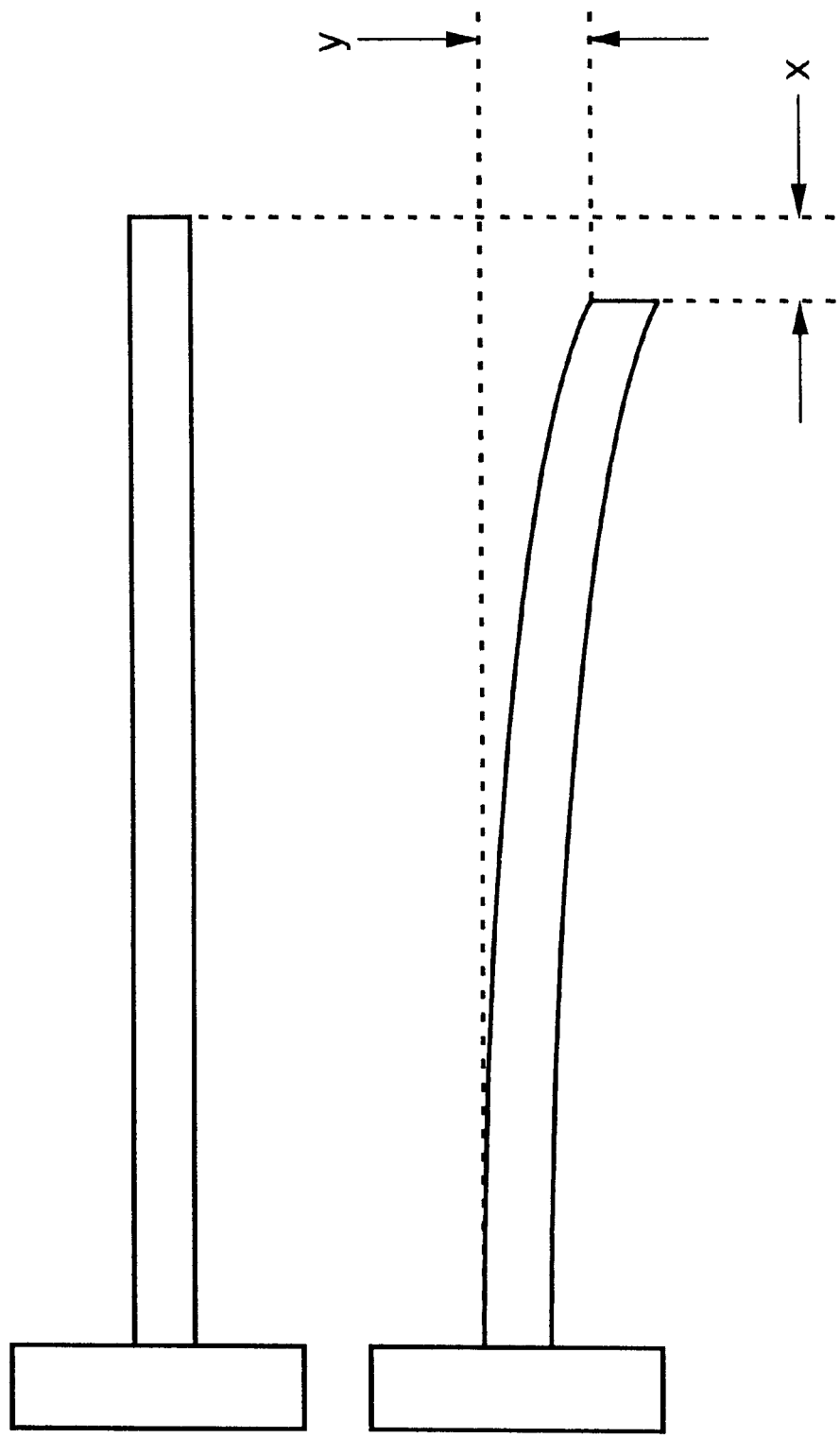
FIG. 5 depicts x and y-axis displacement when a fiber is subjected to a displacement force in the y-axis.

While tedious to solve analytically, it is possible to numerically calculate the amount of cross-talk associated with fibers 18a–c of different lengths. The deflection, Y, of a long fiber at any point x along its length due to a concentrated load, P, at the end of the fiber is given by:

$$Y(x) = \frac{Px^2}{6EI}(3L - x), \quad (1)$$

where L is the length of the fiber, E is the Young's modulus of the fiber, and I is the moment of inertia of the fiber. The moment of inertia, I, is given by:

$$I = \frac{\pi D^4}{64}, \quad (2)$$

where D is the diameter of the fiber. The deflection, Y(x), of equation (1) is essentially the axial motion of the end of the fiber when the fiber is subjected to a transverse displacement, as shown in FIG. 5.

Recalling that the length of an arc can be calculated from the equation:

$$L = \int_0^b \sqrt{1+[f'(x)]^2}\, dx, \qquad (3)$$

a simple numerical analysis can be conducted that yields the cross-talk as a function of the maximum fiber deflection. The appropriate derivative, f'(x), is given by:

$$\frac{dY}{dx} = \frac{P}{6EI}(6Lx - 3x^2). \qquad (4)$$

Substituting equation (4) into equation (3) yields equation (5) below for the total length of the arc formed by the deflected beam.

$$L = \int_0^b \sqrt{1+\left[\frac{P}{6EI}(6Lx-3x^2)\right]^2}\, dx \qquad (5)$$

The length of any segment dL for a given deflection $Y_{max}$ can be found from the following equation (6), which combines equation (1) and equation (5) for x=L.

$$dL = \int_0^b \sqrt{1+\left[\frac{Y_{max}}{2L^3}(6Lx-3x^2)\right]^2}\, dx \qquad (6)$$

Figure 6:
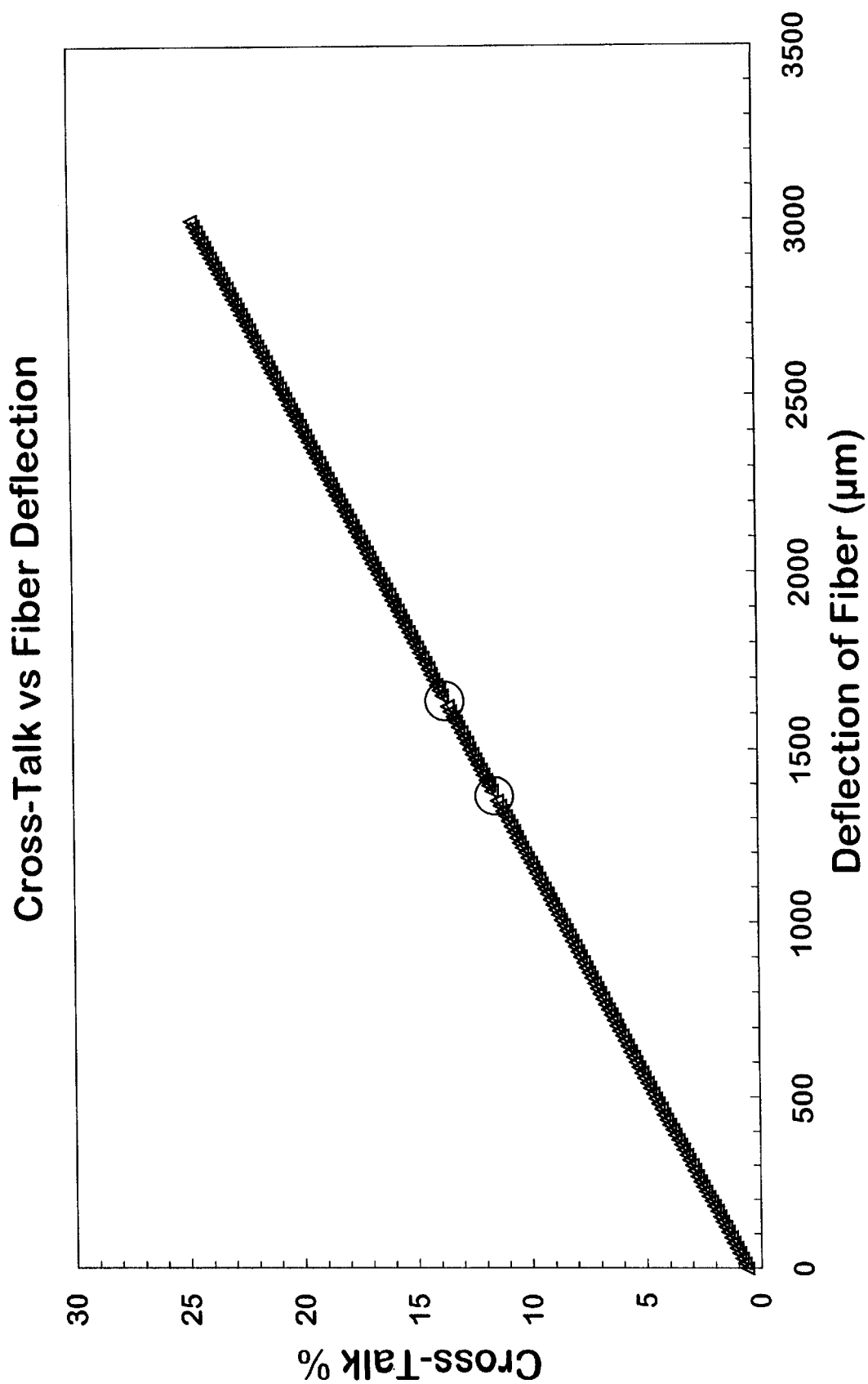
FIG. 6 is a graph depicting calculated cross-talk percentage versus fiber deflection according to a preferred embodiment of the invention.

Equation (6) can be solved numerically by summing the individual dL's for a given $Y_{max}$, until the total length surpasses the original length of the fiber. This allows one to arrive at the plot shown in FIG. 6, from which it may be observed that the model predicts cross-talk on the order of 13–16% (the experimentally determined value) when a fiber of roughly 15 mm in length is deflected by approximately 1.5 mm. This misalignment of the system is certainly possible, and serves to explain the observation that the experimentally measured cross-talk is negative when the system is moving in the air.

Figure 7:
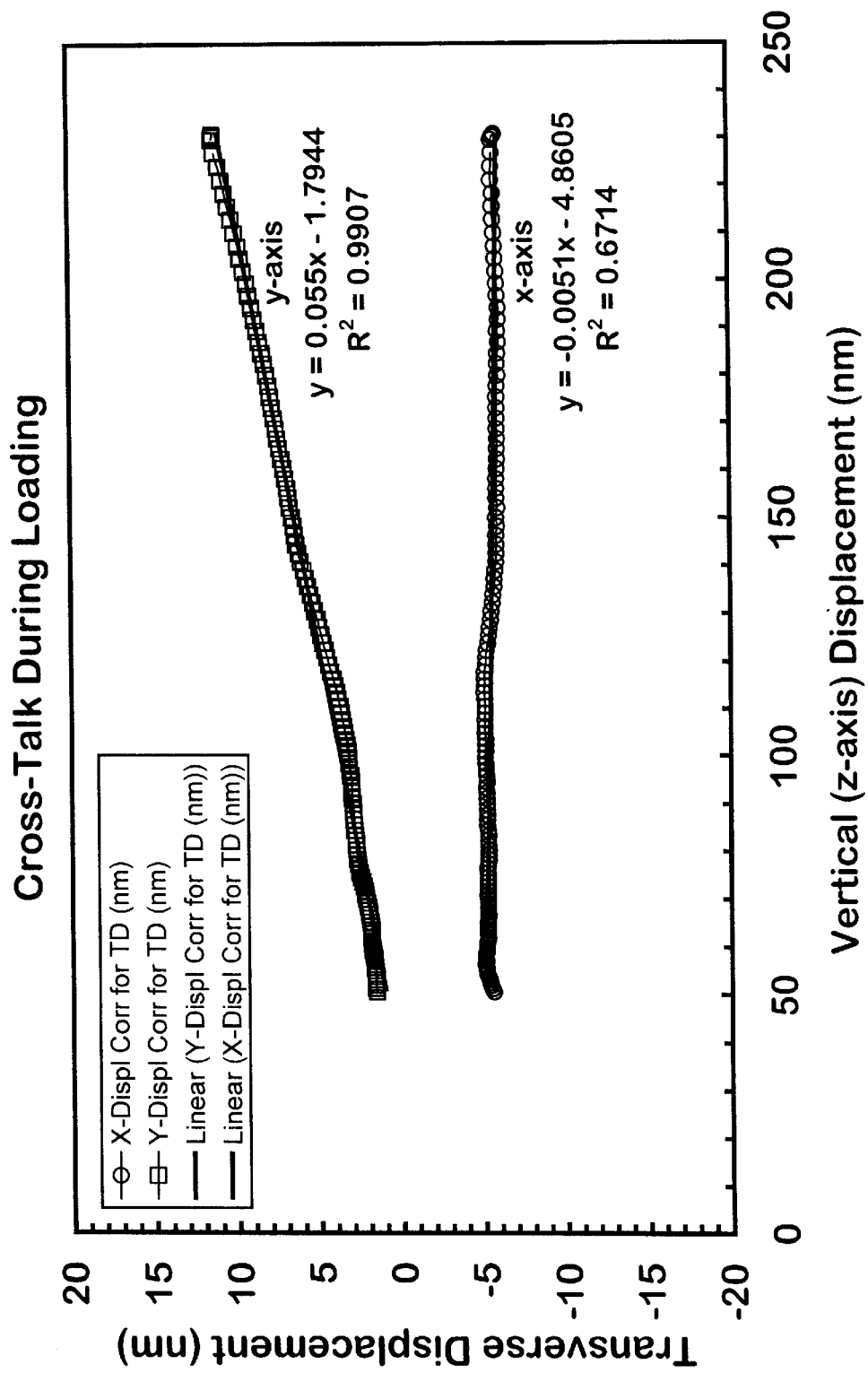
FIG. 7 is a graph depicting transverse displacement versus vertical displacement for x and y axes of the multi-dimensional contact mechanics measurement system, when the contact probe is in contact with a flat fused silica surface, according to a preferred embodiment of the invention.

More important than the amount of cross-talk between the axes while the system is free to move in space is the amount of cross-talk that occurs once the probe 24 has made contact with the surface of interest. FIG. 7 is a plot of the transverse displacement in the x and y-axes, as a function of the controlled z-axis displacement of the probe 24 into the surface. After an initial minor perturbation, the cross-talk is observed to be effectively zero for the x-axis and on the order of 5 percent for the y-axis.

Figure 8:
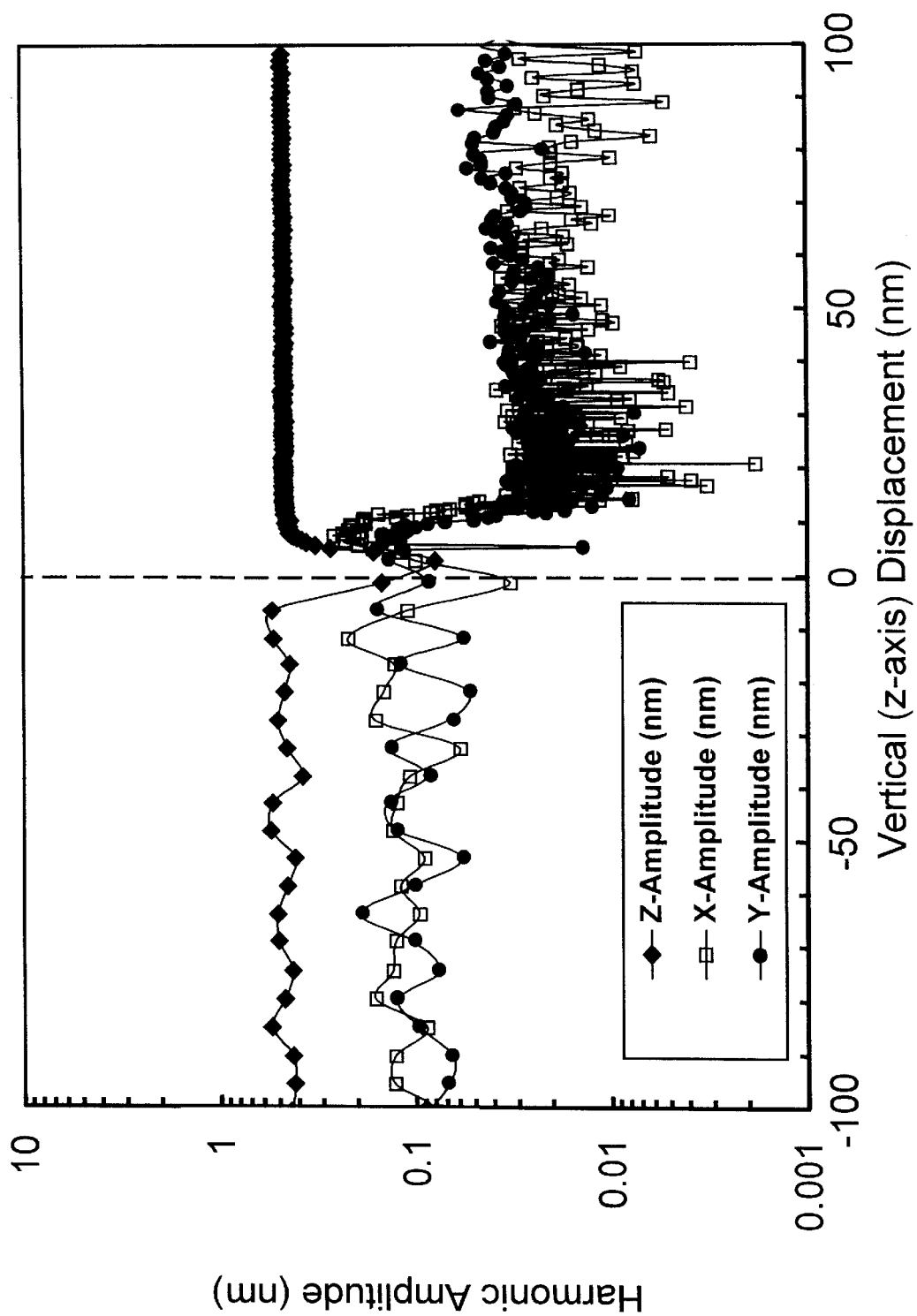
FIG. 8 is a graph depicting harmonic displacement versus vertical displacement at an excitation frequency of 125 Hz for x, y, and z axes of the multi-dimensional contact mechanics measurement system according to a preferred embodiment of the invention.

In addition to moving the individual actuators 14a–c in a quasi-static fashion, it is possible to excite the system 10 harmonically using an oscillator from a lock-in amplifier or similar device. This allows one to determine the displacement response to a specific frequency of harmonic force oscillation. This allows an additional determination of the amount of cross-talk in the system 10 by monitoring the harmonic displacement of two of the axes when the third axis is maintained at a prescribed harmonic displacement amplitude. FIG. 8 is a plot of the harmonic displacement at an excitation frequency of 125 Hz for all three axes. The data cover the time period where the probe 24 is approaching a flat surface of fused silica (negative displacement values), as well as subsequent to contact (positive displacement values). Again, the observed cross-talk between the axes of motion when the system is free to move in the air is observed to be 10–15%. The frequency-specific cross-talk however is observed to be effectively zero once the probe 24 contacts the surface of the material.

A number of properties of the fibers 18a–c used in the system 10 are very important to the effectiveness of the invention in reducing inter-axes cross-talk and the overall performance of the system when measuring small displacements. Two of the most important properties are the lengths of the fibers 18a–c and the coefficient of thermal expansion (CTE) of the fiber material. Essentially, the preferred embodiment of the system 10 represents a compromise between tolerable cross-talk, which is a function of the length of the fiber, and instability due to the thermal expansion of the fibers 18a–c, which is a function of both the length of the fibers 18a–c and their CTE.

When the geometry of the fibers 18a–c is considered in light of the measurement being attempted, it is apparent that a low CTE is a desirable feature of the fibers 18a–c. The system 10 is designed with the goal of measuring displacements on the order of nanometers ($10^{-9}$ m). Thus, any instability in the system that can result in displacements on this order is of great importance. One of these instabilities is the thermal instability in the lengths of the fibers 18a–c if the CTE is too large. This is one reason that silica, having a thermal expansion coefficient of $5\times10^{-7}/°C.$, is the preferred fiber material. With silica, a change in temperature of 0.1° C. results in a change in length of the fiber of only approximately 1 nanometer for a fiber 20 mm in length.

Figure 9:
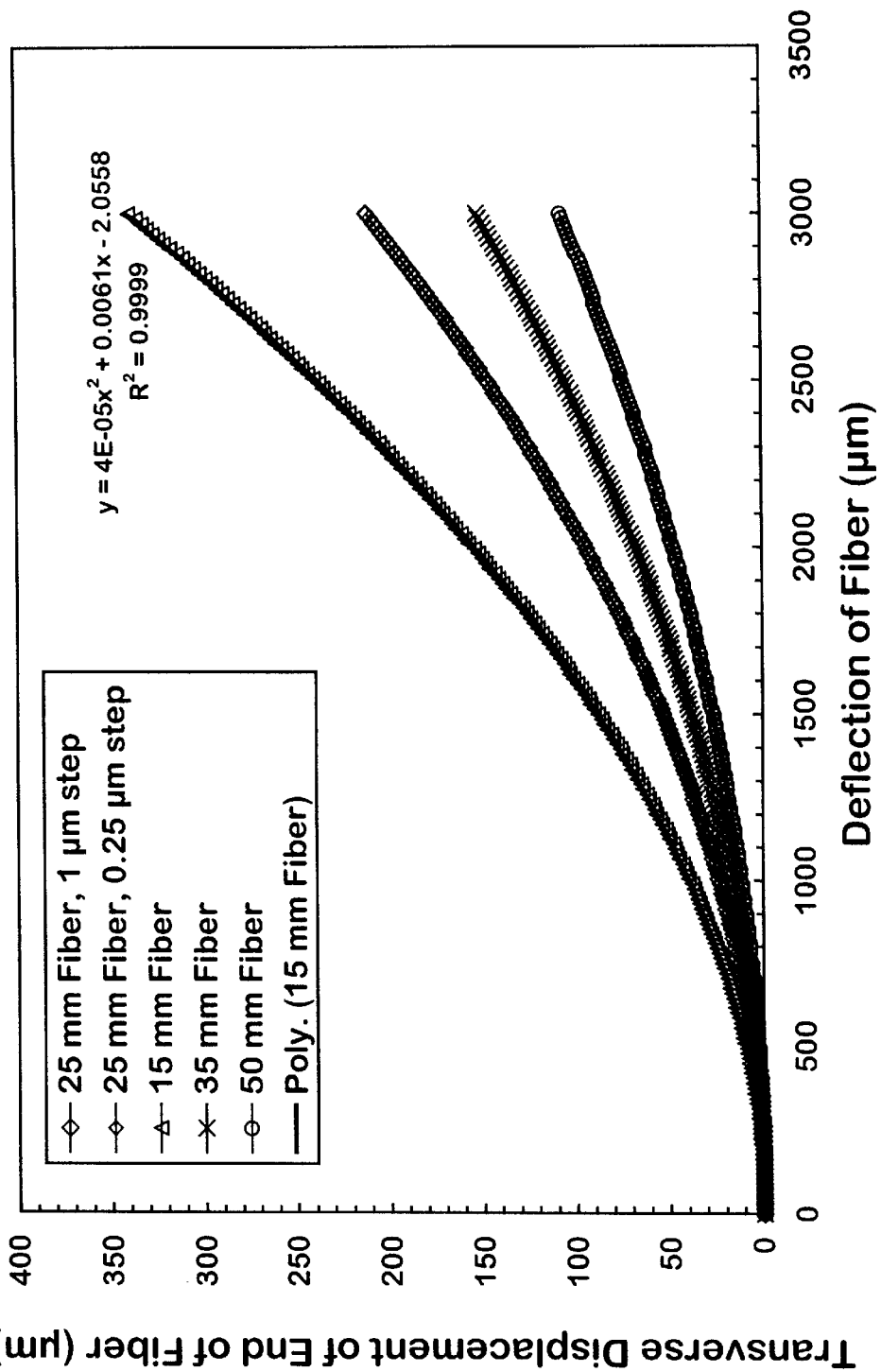
FIG. 9 is a graph depicting calculated transverse displacement of an end of a fiber versus deflection of the fiber for various fiber lengths according to a preferred embodiment of the invention.

Another important consideration is the free length of the fibers 18a–c. The inter-axis cross-talk is driven at least in part by the accommodation of the motion along one axis by the bending and subsequent axial displacement of the two orthogonal fibers. As indicated by equation (6) and as shown FIG. 9, this cross-talk is a function of the lengths of the fibers 18a–c. In theory, the cross-talk can be minimized or made zero by making the fibers 18a–c infinitely long. While being not only impractical, use of infinitely long fibers is also unreasonable based upon the CTE discussion above.

Yet another important consideration is the axial rigidity of the fibers 18a–c compared to their rigidity in bending. By comparing the measured motion stiffness for the three axes prior to and after coupling, it is possible to determine the contribution to the measured stiffness associated with the bending of the respective fibers 18a–c. This allows calculation of an approximate free-length of the fibers 18a–c from the relationship:

$$K_{fiberbending} = \frac{3EI}{L^3}, \qquad (7)$$

where E is the Young's modulus of the fiber material (72 GPa for fused silica), I is the moment of inertia given by equation (2), and L is the fiber length. Table I summarizes these calculations for a preferred embodiment of the fibers 18a–c.

TABLE I

| Fiber | Total Length (mm) | Free Length (mm) | Measured Bending Stiffness (N/m) |
|---|---|---|---|
| 18a | 22.8 | 19 | 45 |
| 18b | 24.1 | 16 | 75 |
| 18c | 24 | 16 | 75 |

The axial stiffness of the fibers 18a–c is expressed as:

$$K_{fiberaxial} = \frac{EA}{L}, \quad (8)$$

where A is the cross-sectional area of the fiber 18a–c, and E and L are as described above. Given this fiber geometry, the ratio of the axial stiffness to the transverse stiffness is approximately $1\times10^4$. It is important to note that for simple fiber geometries, e.g., circular, square or triangular cross-sections, the ratio of the axial stiffness to the bending stiffness for a constant cross-sectional area is maximized for a circular cross-section.

Following is a description of an exemplary use of the system 10 to collect measurement data for a particular thin film material. The material investigated was a ZDOL hard-disk lubricant, in both a bonded and an unbonded condition, on a 50 Å $CN_x$ overcoat on a typical hard disk multi-layer system on a glass substrate. The lubricant had been deposited in thicknesses of 11 Å and 24 Å, and bonded to the $CN_x$ by a specific heat treating process.

After an initial surface finding routine, the probe 24 is positioned at a preset distance above the surface of the material. At this point, an internal control loop of each lock-in amplifier is enabled such that the harmonic displacement amplitude is maintained at about 0.7 nm at a frequency of 125 Hz for all three axes. The probe 24 is then moved toward the surface at a specified displacement rate of 2 nm/s while the force, F, required to maintain the desired displacement oscillation, X, and the phase angle, φ, between the force and displacement is monitored. Once contact is detected, the probe 24 is quasi-statically loaded in the z-direction such that (1/P)(dP/dt) is held constant, where P is the quasi-static normal or z load on the surface. The important measured variable is the force, F, required to maintain a constant harmonic displacement amplitude as the quasi-static load is increased. Ten measurements were run at locations on the surface spaced by 10 microns, and the data was combined to arrive at an average value for each coating. All of the measurements were repeated in a variety of sequences to ensure that there were no effects of the order in which the tests were performed. No attempts were made in these measurements to align the probe 24 with any particular direction in the plane of the sample.

Figure 10:
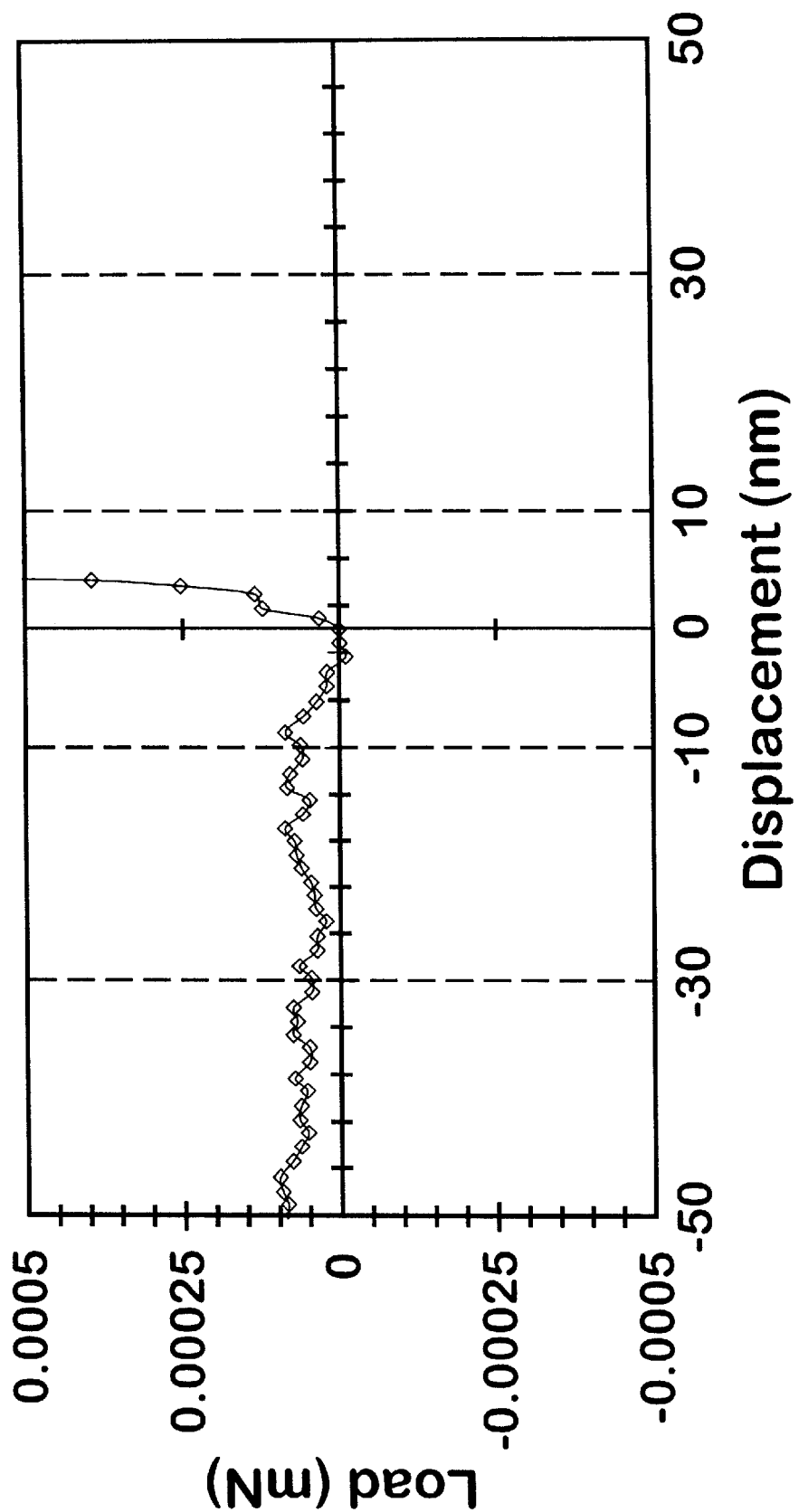
FIG. 10 is a graph depicting normal quasi-static load on a probe versus displacement as the probe approaches and contacts a surface according to a preferred embodiment of the invention.

FIG. 10 is a plot of the normal quasi-static load on the probe 24 versus displacement as it approaches and contacts the surface for a typical measurement on the 24 Å ZDOL bonded lubricant. The curve has been leveled for the effects of the spring that support the system, thereby making the load on the sample effectively zero up until the probe 24 contacts the surface. The appearance of the curve suggests that a small attractive force is present as the probe 24 approaches and contacts the surface. This type of behavior was not unique to any particular sample and was evident to a greater or lesser degree for all of the samples tested.

As the ZDOL lubricant appears to support no load in the Z-direction, it is hypothesized that in all of the samples, the point of contact, as represented in FIG. 10 by the (0,0) point on the curve, is when the probe 24 contacts the $CN_x$. Further evidence for this hypothesis will be discussed as further results are presented.

Figure 11:
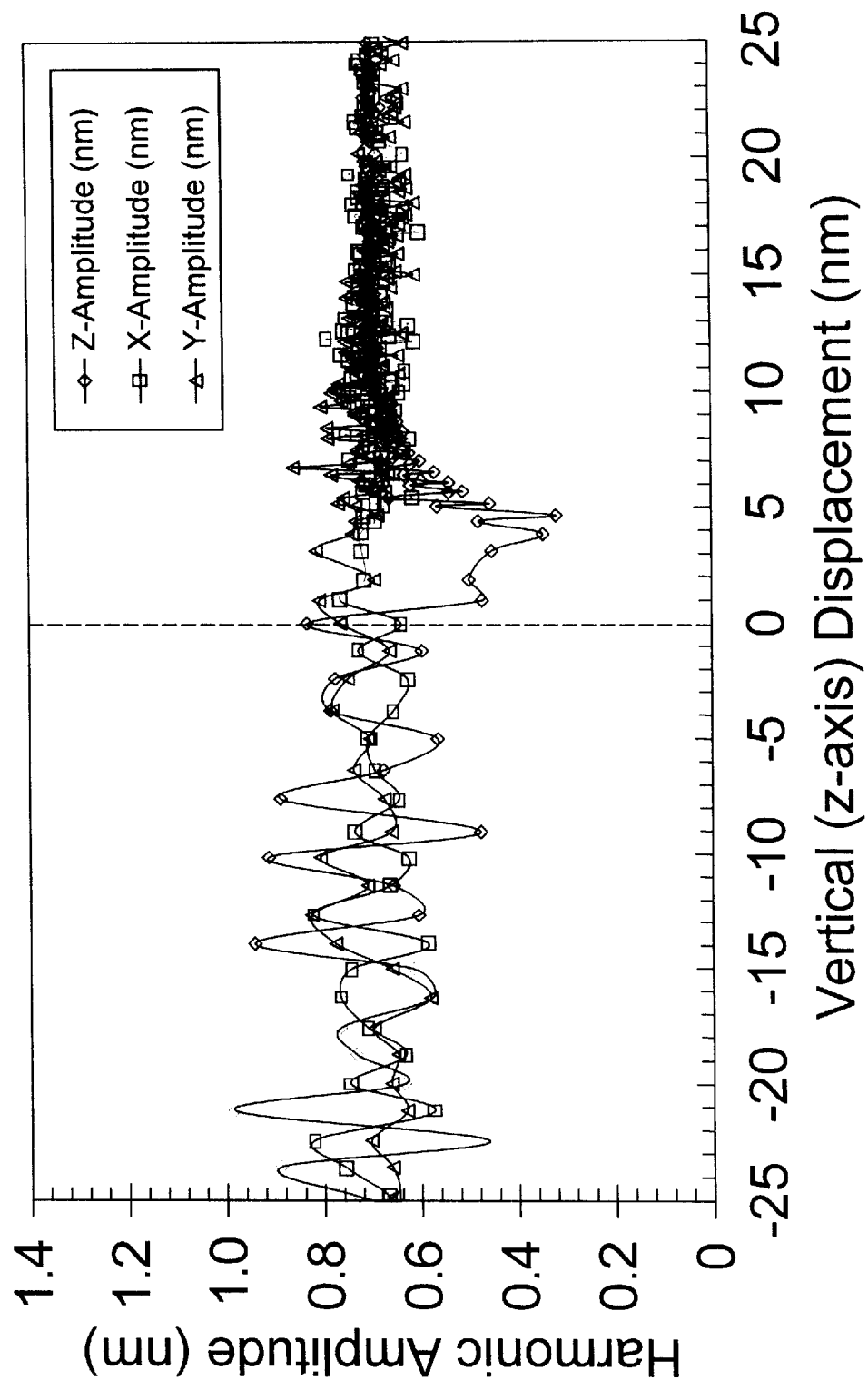
FIG. 11 is a graph depicting the harmonic amplitude of x, y, and z axes versus z-axis displacement as a probe approaches and contacts a surface according to a preferred embodiment of the invention.

FIG. 11 is a plot of the harmonic amplitude of each axis as the probe 24 approaches and contacts the surface. Keep in mind that the amplitude of each axis is controlled by an independent feed-back loop with the harmonic force for each axis. This curve indicates an abrupt change in the harmonic amplitude for the z-axis suggesting not only that the probe 24 has contacted the surface, but also that the mechanical transfer function has changed so abruptly that the displacement amplitude for this particular axis has fallen below the set point until the feedback loop can appropriately respond. It is also noted that there is a lack of a similar response for the x and y-axes, suggesting that the mechanical transfer function has changed much less abruptly for these two axes.

Figure 12:
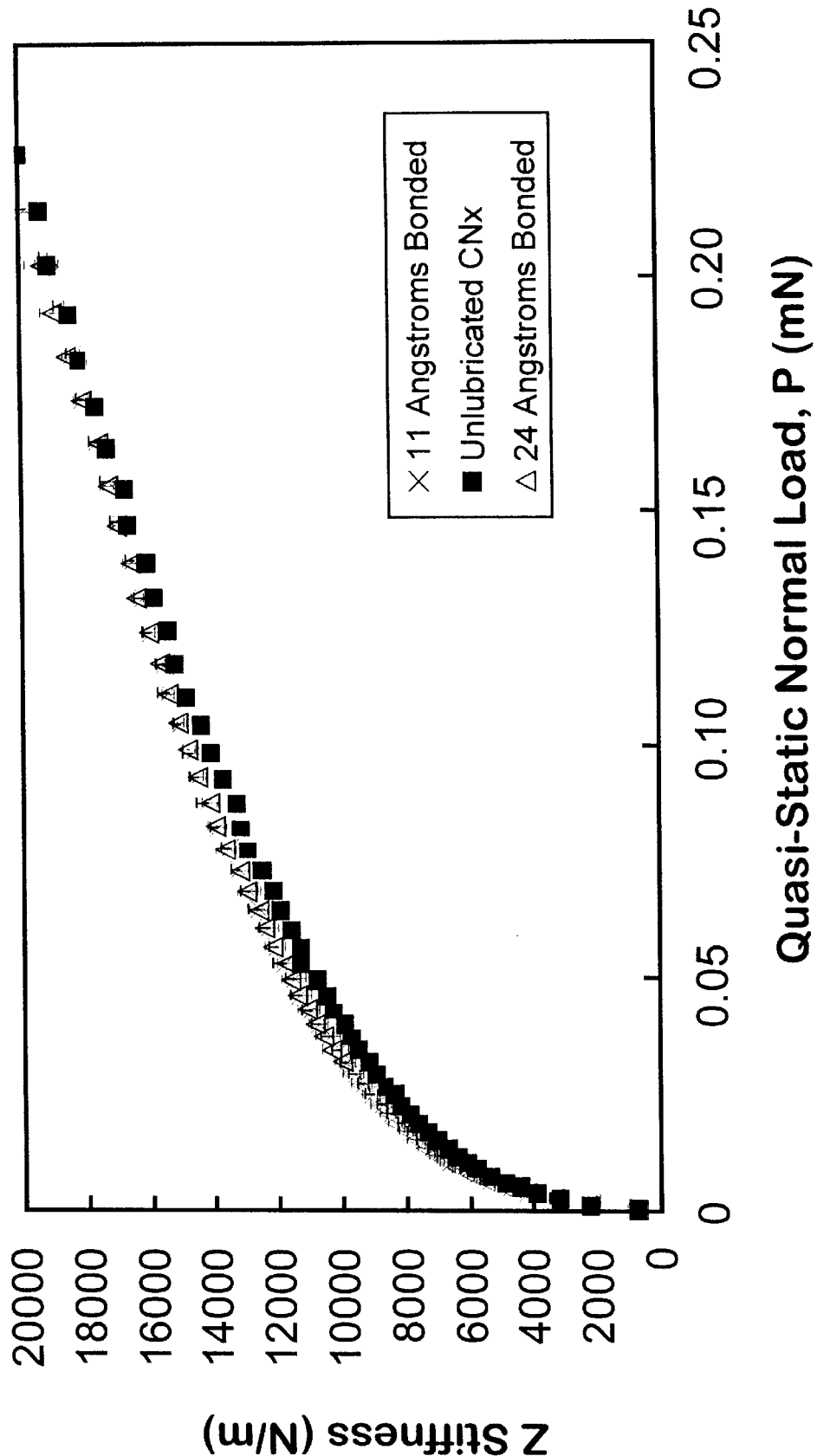
FIG. 12 is a graph depicting harmonic contact stiffness normal to a surface as a function of displacement subsequent to contact with a surface according to a preferred embodiment of the invention.

FIG. 12 is a plot of the harmonic contact stiffness, i.e., the ratio of the harmonic force in the z direction to the resulting harmonic displacement in the z-direction, plotted as a function of displacement subsequent to contact. This is similar to what one would observe using conventional uniaxial indentation. Data for three of the samples, unlubricated $CN_x$, and $CN_x$ lubricated with 11 and 24 Å of the bonded lubricant, are displayed in FIG. 12. As expected, little or no difference is observed in the mechanical response for these three samples. This data supports the hypothesis that the ZDOL lubricant is supporting essentially no load in the z-direction and that in all instances, the measured response in the z-axis is due to the $CN_x$ and the underlying layers. Given the nature of the ZDOL molecules and the tendency for them to align perpendicular to the $CN_x$ surface, this response is not unexpected and serves to show the inability of one-dimensional indentation systems to differentiate between samples of this type.

Figure 13:
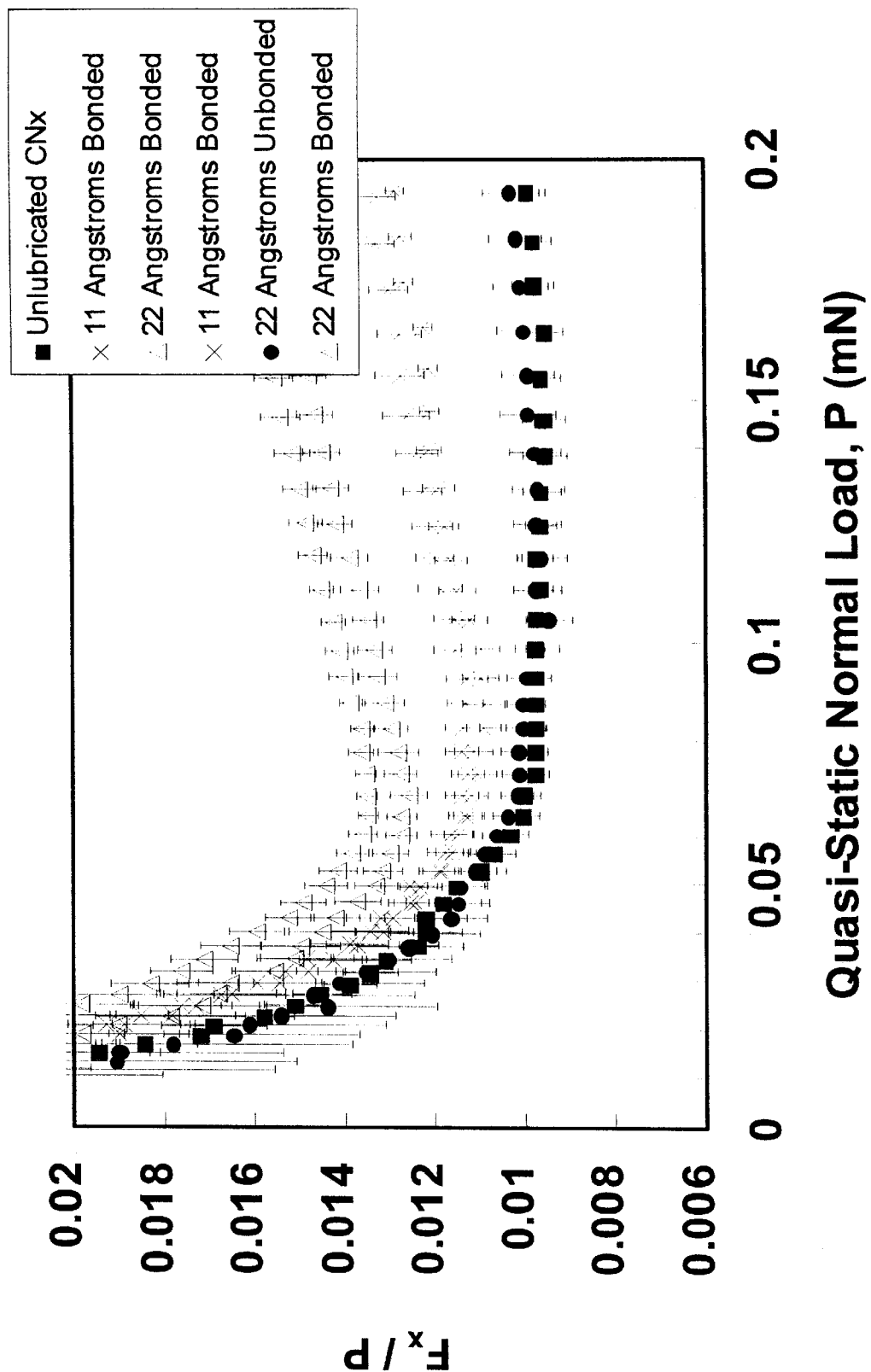
FIG. 13 is a graph depicting harmonic force in the x-direction, normalized by the quasi-static normal load on the probe, required to maintain a particular displacement oscillation versus quasi-static load on the probe according to a preferred embodiment of the invention.

FIG. 13 is a plot of $F_x/P$, which is the harmonic force in the x-direction required to maintain a 0.7 nm displacement oscillation normalized by the quasi-static z-load on the probe 24 versus the quasi-static load on the probe 24. Included in this plot are data from all of the samples measured, with the exception of the unbonded 11 Å ZDOL lubricated $CN_x$, which exhibited a response identical to the unbonded 24 Å ZDOL lubricated sample, and was omitted from the plot for clarity. Data from two different bonded samples of both thicknesses are included to show the reproducibility of the measured response. Each curve represents the average of at least ten measurements on each sample. The data have been discretized based on applied load and subsequently averaged to arrive at the data shown in the plot. These curves indicate that there is little or no measurable difference in the response for the unlubricated $CN_x$ as compared to the $CN_x$ with the thicker, 24 Å unbonded lubricant. One possible explanation for this result is that in both instances the probe 24 is in contact with the $CN_x$ and there is no remaining lubricant layer remaining between the probe 24 and the sample to affect the response. Secondary to this, it is also possible that the unbonded lubricant, which has undergone no heat treating subsequent to its application, will support no shear load as the probe 24 is oscillated in the plane of the sample.

Also shown in FIG. 13 are the data from the two bonded ZDOL lubricants. The response of these two films is observed to be statistically different than one another as well as that of either the unlubricated $CN_x$ sample or the $CN_x$ sample with the unbonded ZDOL lubricant. While the ZDOL is designed to act as a lubricant, it is noted from the plot that the presence of the ZDOL serves to increase the lateral force required to maintain the prescribed displacement oscillation rather than to lower it. This is inconsistent with what is expected for a lubricant layer. This result can perhaps be understood by again considering the initial point of contact as well as the length scale of the in-plane oscillation. As discussed previously in regard to FIGS. 10 and 12, it is hypothesized that the ZDOL lubricant layer supports essentially no load normal to the surface. If this hypothesis is correct, then the measured response for the 1 nm oscillation is perhaps a result of the ZDOL lubricant piling up along the sides of the probe 24 as it is pressed into the surface of the $CN_x$. As the $CN_x$ is expected to behave like a hard film on a compliant substrate, it is conceivable that the $CN_x$ layer deforms elastically in bending as the probe 24 is driven into the surface. As this occurs, the ZDOL continually builds up along the sides of the probe 24, and the force required to maintain this in-plane oscillation increases as the load on the probe 24 is increased. This hypothesis is supported as well by the fact that the lateral force divided by the normal quasi-static force scales with the thickness of the ZDOL; the force being greater for the thicker of the two bonded lubricants. The measured response is thus more closely related to a small-scale, in-plane viscoelastic response than it is a true sliding behavior. This result is supported by a large phase lag during this period between the harmonic force and the harmonic displacement.

Figure 14:
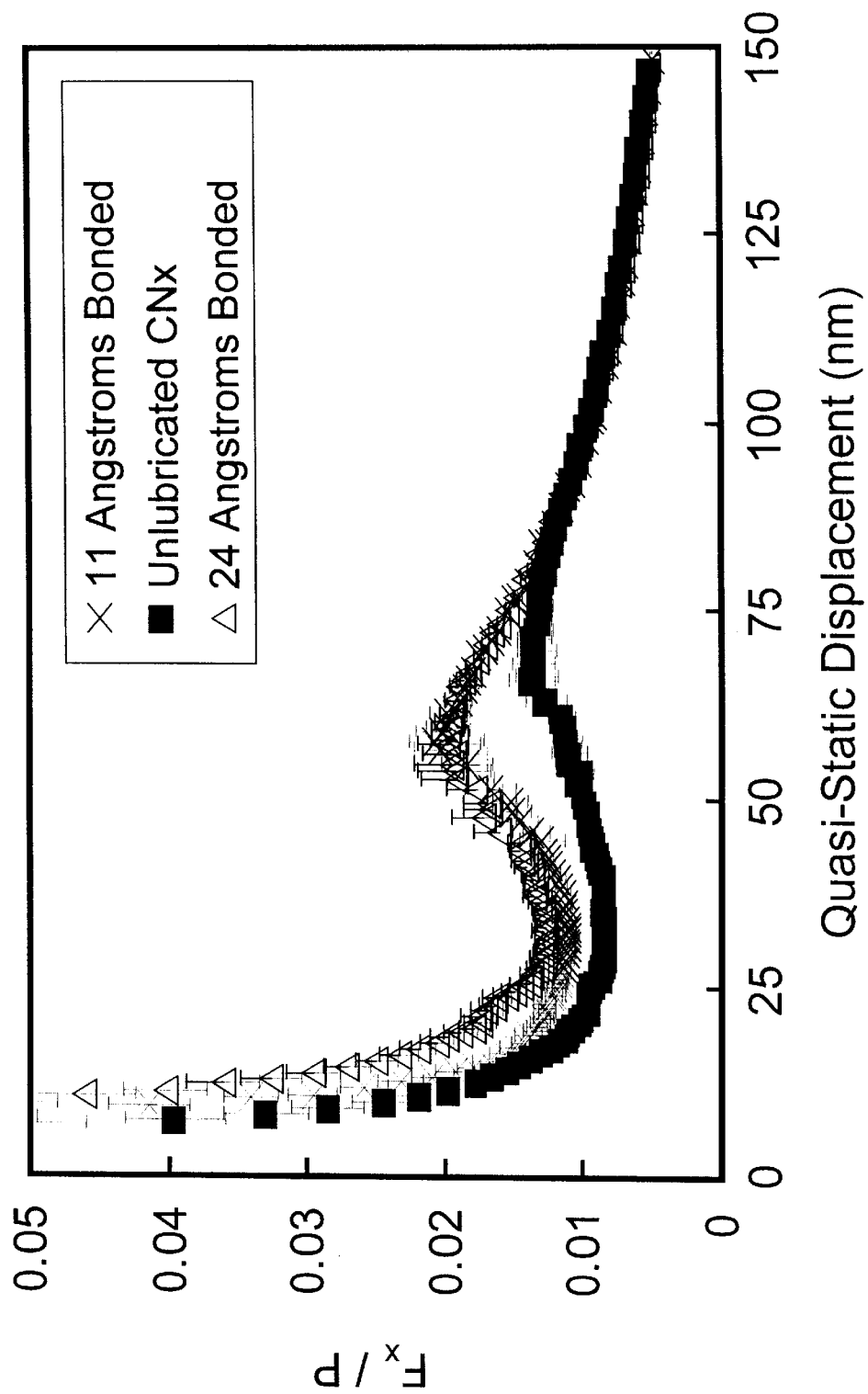
FIG. 14 is a graph depicting harmonic force in the x-direction, normalized by the quasi-static normal load on the probe, required to maintain a particular displacement oscillation versus total probe displacement into the surface according to a preferred embodiment of the invention.

FIG. 14 depicts $F_X/P$ plotted as a function of the total probe displacement into the surface. These measurements were conducted at significantly higher loads in an attempt to investigate the effects of the very thin lubricant layers on larger scale mechanical phenomena for the films. While the lubricant layers are only 11 and 24 Å respectively, the effects of the lubricants on the quantity $F_X/P$ are observed to exist to displacements greater than 75 nm.

The data shown in FIGS. 10–14 indicate among other things that the preferred embodiment of the system 10 has the sensitivity and low level of inter-axial cross-talk required to distinguish between these simple surface coating materials.

Figure 15:
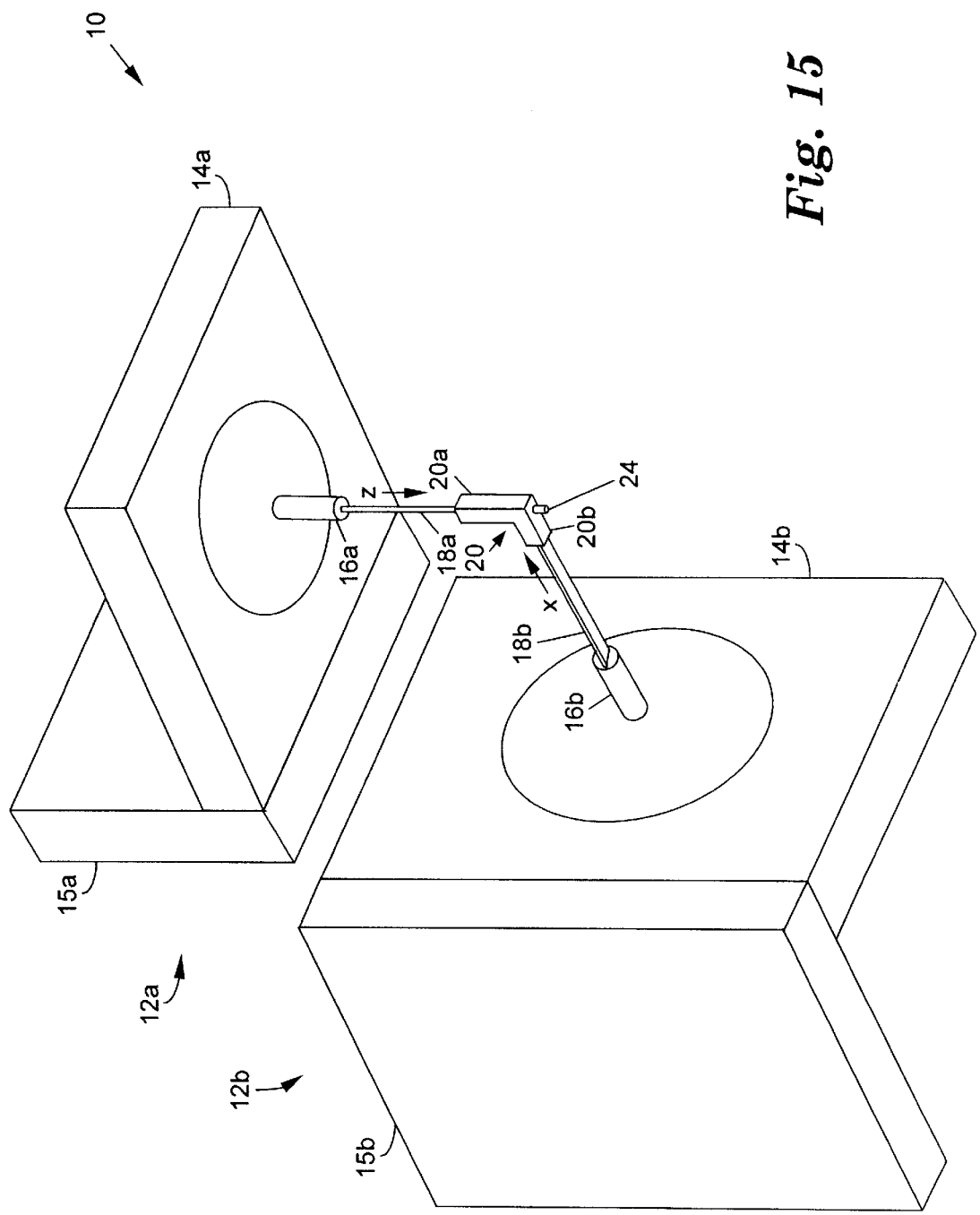
FIGS. 15 and 16 are perspective views of a multi-dimensional contact mechanics measurement system according to an alternative embodiment of the invention.
Figure 16:
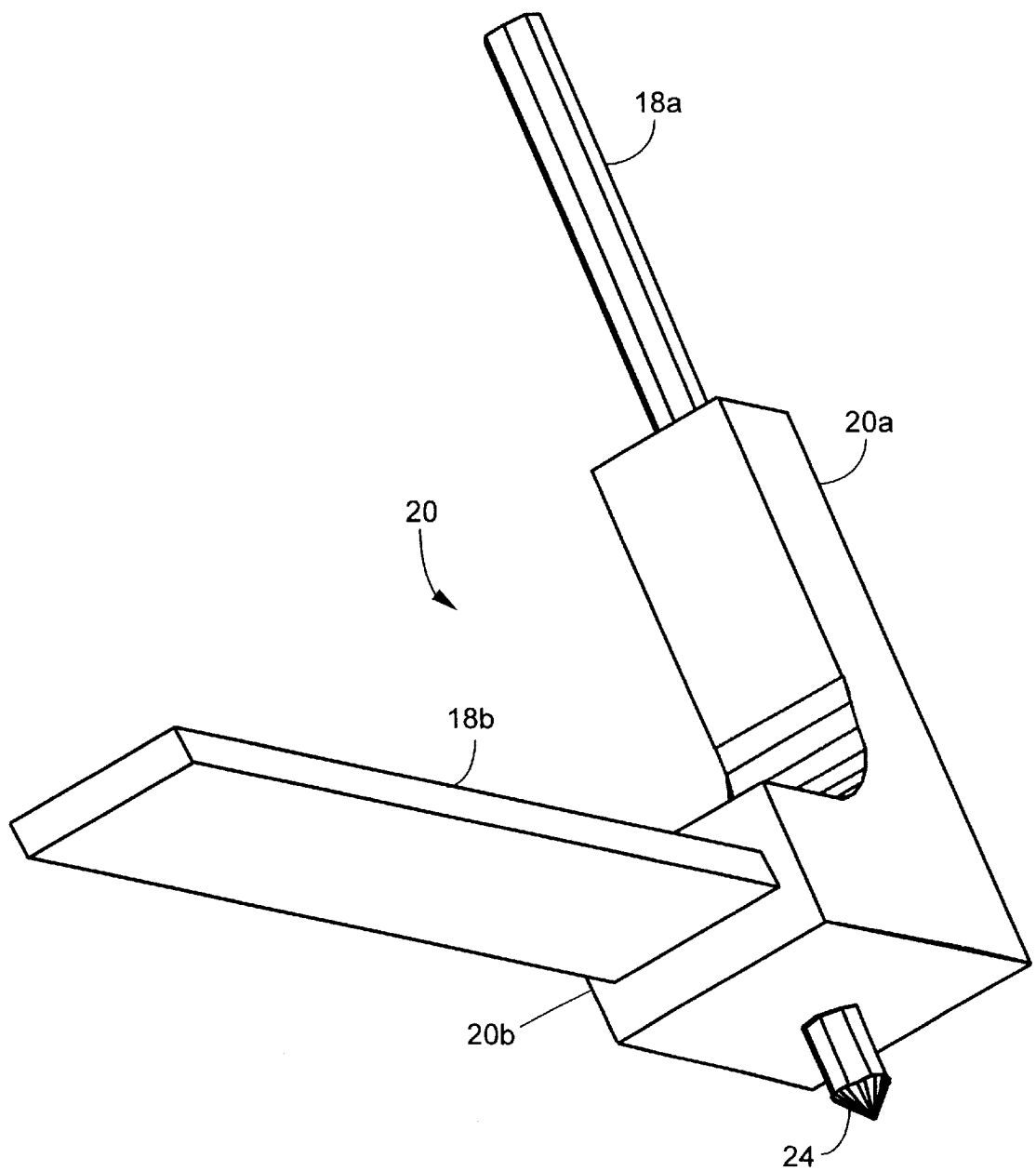

Another embodiment of the system 10 for making measurements in two dimensions, such as x and z, is shown in FIGS. 15 and 16. In this configuration, the second elongate member of the system has the geometry of a long, thin plate 18b. This geometry serves to limit the motion of the system in the x and z directions as the stiffness of the elongate member can be made very large if the width to height ratio of the plate 18b is very high. For instance, if the height, or thickness of the plate 18b is 400 µm and the desired ratio of the stiffness in the z-direction to the stiffness is 10,000, then the width of the plate 18b would preferably be approximately 18.4 mm.

Figure 17:
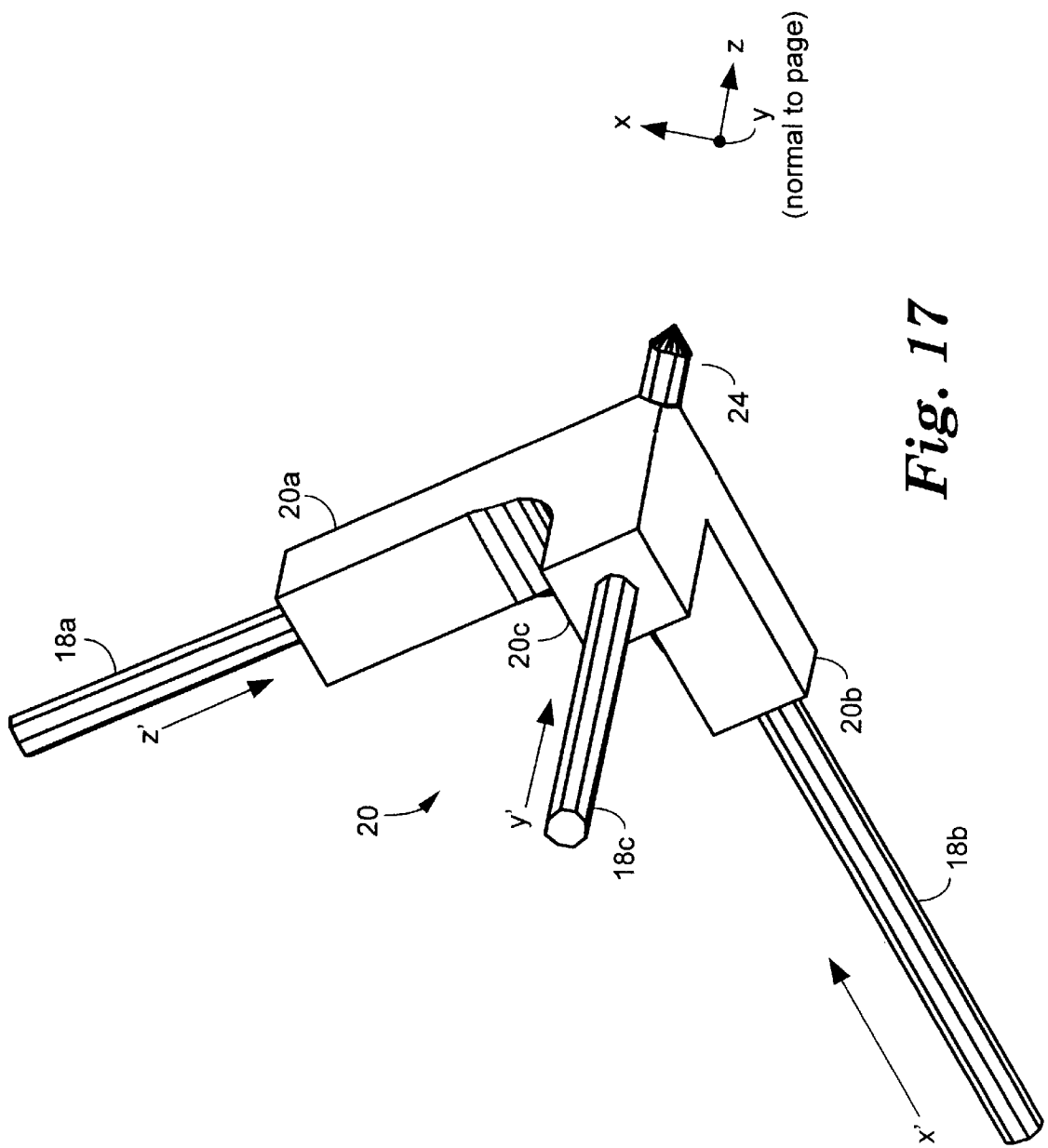
FIG. 17 is a perspective view of a multi-dimensional contact mechanics measurement system according to an alternative embodiment of the invention.

In an alternative embodiment, as depicted in FIG. 17, the members 18a, 18b, and 18c are oriented at an angle of approximately 45 degrees with respect to a measurement surface. In this embodiment, the probe 24 is positioned on the outside corner of the coupler 20 where the members 20a–c of the coupler 20 are joined, and is oriented at an angle of approximately 135 degrees with respect to each of the elongate members 18a–18c. Thus, the invention is not limited to making measurements in the x, y, and z axes only, where the z axis is normal to the measurement surface. As shown in FIG. 17, the invention may also be used to make measurements in x', y', and z' axes that are rotated, such as by 45 degrees, relative to the x, y, and z axes.

It is contemplated, and will be apparent to those skilled in the art from the preceding description and the accompanying drawings that modifications and/or changes may be made in the embodiments of the invention. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. A multidimensional surface mechanics measurement system for applying forces to a surface or imposing displacements of a surface in multiple directions, and for minimizing coupling between the forces or displacements so applied, the system comprising:

a first elongate fiber extending in a first axial direction, and having first and second ends;

a second elongate fiber extending in a second axial direction that is substantially orthogonal to the first axial direction, and having first and second ends; and a coupler for coupling the first elongate fiber to the second elongate fiber, the coupler attached to the first end of the first elongate fiber and to the first end of the second elongate fiber;

a first actuator attached to the first elongate fiber adjacent the second end of the first elongate fiber for applying a first axial force or imposing a first axial displacement to the first elongate fiber in the first axial direction;

a second actuator attached to the second elongate fiber adjacent the second end of the second elongate fiber for applying a second axial force or imposing a second axial displacement to the second elongate fiber in the second axial direction; and a probe connected to the coupler having a contact point for interacting with the surface.

2. The multidimensional surface mechanics measurement system of claim 1 where the first axial direction is substantially normal to the surface.

3. The multidimensional surface mechanics measurement system of claim 1 where the first axial direction is oriented at an angle of approximately 45° with respect to the surface.

4. The multidimensional surface mechanics measurement system of claim 1 further comprising:

a third elongate fiber extending in a third axial direction that is substantially orthogonal to the first and second axial directions, and having first and second ends;

the coupler attached to the first end of the third elongate fiber; and a third actuator attached to the third elongate fiber adjacent the second end of the third elongate fiber for applying a third axial force or imposing a third axial displacement to the third elongate fiber in the third axial direction.

5. The multidimensional surface mechanics measurement system of claim 4 further comprising:

the coupler having:

a third rigid member aligned with the third axial direction; and a third shaft within the third rigid member into which the first end of the third elongate fiber is inserted, the third shaft having a third inside diameter and a third depth; and the third elongate fiber having a third outside diameter of substantially equal to but no greater than the third inside diameter of the third shaft.

6. The multidimensional surface mechanics measurement system of claim 1 wherein the first elongate fiber has a first axis in the first axial direction, the first axis intersecting the contact point of the probe.

7. The multidimensional surface mechanics measurement system of claim 1 further comprising:

the first elongate fiber having a first axial stiffness in the first axial direction and a first transverse stiffness in a direction transverse to the first axial direction, and where a ratio of the first axial stiffness to the first transverse stiffness ranges from approximately 3,000 to 30,000; and the second elongate fiber has a second axial stiffness in the second axial direction and a second transverse stiffness in a direction transverse to the second axial direction, and where a ratio of the second axial stiffness to the second transverse stiffness ranges from approximately 3,000 to 30,000.

8. The multidimensional surface mechanics measurement system of claim 1 wherein the first and second elongate fibers each have a free length and a diameter, and wherein a ratio of free length to diameter ranges from about 37 to about 45.

9. The multidimensional surface mechanics measurement system of claim 1 wherein the first and second elongate fibers each have a free length of approximately 12.7 mm to 25.4 mm, and a diameter of approximately 400 µm to 440 µm.

10. The multidimensional surface mechanics measurement system of claim 1 wherein the first and second elongate fibers are formed from a material having a Young's modulus of approximately 10 GPa to 500 GPa.

11. The multidimensional surface mechanics measurement system of claim 1 wherein the first and second elongate fibers are formed from a material having a coefficient of thermal expansion of approximately $1.0 \times 10^{-7}$ m/°C. to $1.0 \times 10^{-5}$ m/°C.

12. The multidimensional surface mechanics measurement system of claim 1 wherein the first and second elongate fibers each comprise one or more fused silica fibers.

13. The multidimensional surface mechanics measurement system of claim 1 further comprising:
   the coupler having:
      a first rigid member aligned with the first axial direction;
      a second rigid member aligned with the second axial direction;
      a first shaft within the first rigid member into which the first end of the first elongate fiber is inserted, the first shaft having a first inside diameter and a first depth; and
      a second shaft within the second rigid member into which the first end of the second elongate fiber is inserted, the second shaft having a second inside diameter and a second depth;
   the first end of the first elongate fiber having a first outside diameter of substantially equal to but no greater than the first inside diameter of the first shaft; and
   the first end of the second elongate fiber having a second outside diameter of substantially equal to but no greater than the second inside diameter of the second shaft.

14. The multidimensional surface mechanics measurement system of claim 13 wherein a ratio of the first depth to the first inside diameter of the first shaft is no less than approximately 4.8, and a ratio of the second depth to the second inside diameter of the second shaft is no less than approximately 4.8.

15. The multidimensional surface mechanics measurement system of claim 13 wherein the first and second depths are approximately 1 mm to 3 mm.

16. The multidimensional surface mechanics measurement system of claim 13 wherein the first and second inside diameters are approximately 430 µm to 440 µm.

17. A multidimensional surface mechanics measurement system for applying forces to a surface or imposing displacements of a surface in multiple directions, and for minimizing coupling between the forces or displacements so applied, the system comprising:
   a first elongate fiber extending in a first axial direction that is substantially normal to the surface, having a first axial stiffness in the first axial direction, and having a first transverse stiffness in a direction transverse to the first axial direction, where a ratio of the first axial stiffness to the first transverse stiffness ranges from approximately 3,000 to 30,000, and having a first end with a first outside diameter;
   a second elongate fiber extending in a second axial direction that is substantially orthogonal to the first axial direction, having a second axial stiffness in the second axial direction, having a second transverse stiffness in a direction transverse to the second axial direction, where a ratio of the second axial stiffness to the second transverse stiffness ranges from approximately 3,000 to 30,000, and having a first end with a second outside diameter;
   a coupler for coupling the first elongate fiber to the second elongate fiber, comprising:
      a first rigid member aligned with the first axial direction, the first rigid member having a first shaft with a first inside diameter of no less than the first outside diameter of the first end of the first elongate fiber; and
      a second rigid member coupled to the first rigid member and aligned with the second axial direction, the second rigid member having a second shaft with a second inside diameter of no less than the second outside diameter of the first end of the second elongate fiber; and
   a probe connected to the coupler having a contact point for interacting with the surface.

18. The multidimensional surface mechanics measurement system of claim 17 further comprising:
   a third elongate fiber extending in a third axial direction that is substantially orthogonal to the first and second axial directions, having a third axial stiffness in the third axial direction, having a third transverse stiffness in a direction transverse to the third axial direction, where a ratio of the third axial stiffness to the third transverse stiffness ranges from approximately 3,000 to 30,000, and having a first end with a third outside diameter; and
   the coupler further for coupling the third elongate fiber to the first and second elongate fibers, the coupler further comprising a third rigid member coupled to the first and second. rigid members and aligned with the third axial direction, the third rigid member having a third shaft with a third inside diameter of no less than the third outside diameter of the first end of the third elongate fiber.

19. A multidimensional surface mechanics measurement system for applying forces to a surface or imposing displacements of a surface in multiple directions, and for minimizing coupling between the forces or displacements so applied, the system comprising:
   a first elongate fiber extending in a first axial direction that is substantially normal to the surface, and having first and second ends;
   a first actuator coupled to the first elongate fiber adjacent the second end of the first elongate fiber for applying a first axial force to the first elongate fiber in the first axial direction;
   a second elongate fiber extending in a second axial direction that is substantially orthogonal to the first axial direction, and having first and second ends;
   a second actuator coupled to the second elongate fiber adjacent the second end of the second elongate fiber for applying a second axial force to the second elongate fiber in the second axial direction; and a coupler for coupling the first elongate fiber to the second elongate fiber, comprising:
  means for attaching the first elongate fiber to the coupler adjacent the first end of the first elongate fiber; and
  means for attaching the second elongate fiber to the coupler adjacent the first end of the second elongate fiber, whereby the second elongate fiber is disposed substantially orthogonal to the first elongate fiber; and a probe connected to the coupler having a contact point for interacting with the surface.

20. The multidimensional surface mechanics measurement system of claim 19 further comprising:

a third elongate fiber extending in a third axial direction that is substantially orthogonal to the first and second axial directions, and having first and second ends;

a third actuator coupled to the third elongate fiber adjacent the second end of the third elongate fiber for applying a third axial force to the third elongate fiber in the third axial direction; and the coupler further for coupling the third elongate fiber to the first and second elongate fibers, the coupler further comprising:
  means for attaching the third elongate fiber to the coupler adjacent the first end of the third elongate fiber; and
  means for attaching the third elongate fiber to the coupler adjacent the first end of the third elongate fiber, whereby the third elongate fiber is disposed substantially orthogonal to the first and second elongate fibers.

21. A multidimensional surface mechanics measurement system for applying forces to a surface or imposing displacements of a surface in multiple directions, and for minimizing coupling between the forces or displacements so applied, the system comprising:

an elongate fiber extending in a first axial direction, and having first and second ends;

an elongate thin plate extending in a second axial direction that is substantially orthogonal to the first axial direction, and having first and second ends; and a coupler for coupling the first end of the elongate fiber to the first end of the elongate plate; and a probe connected to the coupler having a contact point for interacting with the surface.

* * * * *